United States Patent
Day

(10) Patent No.: US 6,200,605 B1
(45) Date of Patent: Mar. 13, 2001

(54) ANTIFLATULENT COMPOSITION

(76) Inventor: Charles E. Day, 1434 Sunbeam Rd., Leitchfield, KY (US) 42754

( * ) Notice: Subject to any disclaimer, the term of this patent is extended or adjusted under 35 U.S.C. 154(b) by 0 days.

(21) Appl. No.: 09/182,695

(22) Filed: Oct. 29, 1998

Related U.S. Application Data

(60) Provisional application No. 60/064,407, filed on Oct. 30, 1997.

(51) Int. Cl.⁷ .................... A61K 9/14; A61K 9/00
(52) U.S. Cl. ........................... 424/484; 424/400
(58) Field of Search ...................... 424/400, 484

(56) References Cited

U.S. PATENT DOCUMENTS 4,327,076 * 4/1982 Puglia et al. .................. 424/38
5,498,426 * 3/1996 Wilson et al. ................. 424/602

* cited by examiner

*Primary Examiner*—Thurman K. Page
*Assistant Examiner*—Todd D. Ware

(57) ABSTRACT

An antiflatulent composition is disclosed which comprises a polysaccharide and a preservative. The composition is useful to control gas formation at the site of generation of flatulence.

4 Claims, No Drawings

ANTIFLATULENT COMPOSITION

CROSS-REFERENCE TO RELATED APPLICATIONS

This application incorporates by reference the applicant's U.S. Provisional application Ser. No. 60/064,407, filed Oct. 30, 1997, from which priority is claimed.

FIELD OF THE INVENTION

The invention relates to a composition useful as an antiflatulent dietary supplement.

DESCRIPTION OF THE RELATED ART

Flatulence is a normal human excretory function socially stigmatized in the United States. Flatulence is the result of the production of gases in the large intestine by anaerobic microbes, primarily bacteria, that are nourished by the contents of the intestinal lumen. Other than the bacteria themselves, which can number as great as one trillion per gram of colonic lumenal contents, the contents of the lumen of the large intestine include, aside from water and ions and other minor components, foodstuffs not digested during prior transit through the proximal portions of the alimentary canal: the mouth, esophagus, stomach and small intestine. It is these otherwise undigested lumenal contents which the microbes themselves may digest. End-products of the metabolism of these contents by the anaerobic microbes include various gases, including $H_2$, $CH_4$, etc. and short-chain fatty acids (SCFAs) such as acetic, propionic, and butyric acids. One of the primary loci of absorption of SCFAs out of the lumen and into colonic epithelia is the proximal portion of the colon, i.e. the cecum and ascending (right) colon. Gases are excreted through the lungs or via the external anal sphincter (EAS). Digestive processes in the colon are reviewed in: Cummings J H, Macfarlane G T (1991) The control and consequences of bacterial fermentation in the human colon. *Journal of Applied Bacteriology* 70, 443–459; Nordgaard I, Mortensen P B (1995) Digestive processes in the human colon. *Nutrition* 11, 37–45; Gibson G R, Roberfroid M B (1995) Dietary modulation of the human colonic microbiota: introducing the concept of prebiotics. *Journal of Nutrition* 125, 1401–1412.

Previous inventions to relieve flatulence have in general been medications based upon compounds such as simethicone that lower the surface tension of gas bubbles evolved in the bowel lumen, hence lessening individual bubble volume and easing passage. Some such compositions are described in U.S. Pat. Nos. 4,127,650, 5,599,577, and 5,612,054. Useful as such inventions may be, they do not address the root cause of flatulence, i.e. the production of gas by the resident microbes. The use of a microbial galactosidase to prevent flatulence is known in the art but is limited in its potential effectiveness to flatulence caused by the fermentation of galactose-containing oligosaccharides. Moreover, such enzymatic preventatives are limited in their effectiveness by the ability of the enzyme to withstand the rigors of the environment of the stomach and the small intestine and by the uncertain probability that enzyme and substrate will productively collide.

None of the aforementioned inventions acts directly on the microbes that are directly responsible for gas production.

Synthesis and activity of sequential metabolic enzyme systems such as those that engage in anaerobic (fermentative) metabolism is in general regulated by certain end-products of the action of such metabolic pathways. If enzyme synthesis itself is regulated, the process is called repression; if enzyme activity alone, then feedback inhibition.

In the case of colon lumen microbes, the regulatory milieu is complicated by the fact that gases are excreted through the lungs or via the EAS while SCFAs are absorbed primarily in the proximal segments of the large intestine. Thus the microbes often continue to produce gas as long as a suitable food source is available, since end-products of metabolism do not always accumulate but instead can be released into the external environment or absorbed into the body.

BRIEF SUMMARY OF THE INVENTION

So to address a long-felt need for an effective antiflatulent, the inventor envisioned a supplement to the normal human diet which would comprise a food preservative, for example a food preservative generally recognized as safe that is also a metabolic end-product of microbial fermentation. (Preservatives generally recognized as safe are enumerated, and conditions of their approved use are listed, in 21 CFR 582, which is incorporated by reference.) Among such compounds are traditional food preservatives such as vinegar, consisting primarily of acetate and a fraction of SCFAs, in use for thousands of years to prevent food spoilage.

However, the ingestion of vinegar as such has not been shown to confer relief of flatulence.

Another preservative occurring as a metabolite in nature is benzoate. Ingestion of meaningful quantities of benzoate was found by the present inventor to induce severe and acute diuresis which was concluded to be potentially harmful. No antiflatulent property was noted.

From the observation of benzoate-induced diuresis, and from benzoate's lack of noticeable antiflatulent activity when ingested alone, it was inferred that a large proportion of benzoate must have been absorbed before it could arrive at the colon.

Hence a dietary supplement formulation was envisioned and developed that would include an end product of microbial fermentative metabolism safe for human consumption but not capable of being absorbed to a large degree before arriving at the lumen of the distal portions of the colon.

A composition consisting of citrus pectin and calcium propionate was developed and tested. The composition possessed considerable antiflatulent activity.

The utilization of a dietary supplement composition consisting of substances generally recognized as safe in order to diminish flatulence had not been known in the art. Such a composition proved useful to address a long-felt need for an effective antiflatulent. Related art did not in any way contemplate the use of, for instance, SCFAs as antiflatulents.

The invention is to be distinguished from drugs known in related art such as antibiotics which may kill microbes selectively or indiscriminately or which inhibit the synthesis of certain classes of macromolecules by microbes resident in the intestinal lumen. The current invention does not relate to such drugs since it has to do with the presentation of relatively non-toxic presumptive products of their own metabolism to anaerobic microbes resident in the colonic lumen.

The invention is also to be distinguished from so-called colonic delivery systems, such as those described in U.S. Pat. No. 5,525,634, that present drugs to the intestinal epithelial cells for absorption into the body. The current invention does not relate to such devices since it has to do with the presentation of relatively non-toxic presumptive products of their own metabolism to anaerobic microbes resident in the colonic lumen, not for absorption into the body.

The art teaches away from antiflatulent use of SCFAs. For example, while SCFAs were noted as being present in normal human feces, SCFAs administered in solution were shown to be rapidly absorbed from the colon. McNeil, N I et al. (1978) Short chain fatty acid absorption by the human large intestine. Gut 19, 819–822. The use of SCFAs, preservatives or microbistats (i.e., compositions used not to kill but rather to slow or control the growth of microbes) to manipulate flatulence has therefore not been contemplated in the art.

It should be noted that flatulence is a common adverse event associated with a variety of important classes of medications, including proton pump inhibitors (Langtry H D & Wilde M I, *Drugs* 56, 447), HIV protease inhibitors (Moyle G J et al., *J Clin Pharmacol* 38, 736), nonsteroidal anti-inflammatory drugs (Bocanegra T S et al., *J Rheumatol* 25, 1602), and alpha-glucosidase inhibitors (Chan J C et al., *Diabetes Care* 21, 1058). From these reports, all published in 1998, one can justifiably infer that there is a need for an antiflatulent which the known art has not addressed.

DETAILED DESCRIPTION OF THE INVENTION

The usefulness of the antiflatulent dietary supplement was demonstrated in an exemplary 50 year-old individual who regularly consumes a high fiber diet consisting of whole grain breads and baked goods, bran cereals, and fresh fruits, especially apples, and vegetables. Because of the high dietary fiber intake this individual produces copious quantities of intestinal gas which significantly increase above normal levels the number of daily flati. For baseline information the individual maintained a daily diary of all ingested substances and time of their ingestion. Also, the time of each flatus, defecation, and urination was recorded for 21 days, to yield a compilation of data which will hereinafter be referred to as a flatulogram.

The most striking feature of this flatulogram is the marked 48 hour periodicity with diurnal peak to trough intervals for frequency of flati. During this 21 day baseline period the daily average for flati frequency was 19. The peak average was 32, and the trough average was 9.

Based on the dietary history and the marked periodicity of the baseline flatulogram, it was hypothesized that the flatulogram may reflect classical feedback inhibition of microbial metabolic activity. Because of the high dietary fiber, especially pectins, and the high peak fermentation rates as reflected in flati frequency, it can reasonably be assumed that production rates of SCFAs were elevated. Since a primary SCFA of intestinal microbial degradation of pectins is propionic acid, and since propionates are microbistatic, it was further hypothesized that propionate may be a mediator of flati frequency periodicity. Under conditions of low fecal propionate concentration microbial fermentation of dietary fibers accelerates until inhibitory concentrations of propionate are produced by the fermentation process. As propionate and other SCFAs are removed by intestinal absorption and microbial utilization, SCFA concentrations are reduced below inhibitory levels to allow microbial fermentation to accelerate once again. This cycle of fermentative generation of product inhibitors, repression, metabolic removal of SCFA inhibitors and derepression could be a factor in explaining the 48 hour flati periods in this person consuming a high fiber diet.

While not wishing to be bound by theory, the inventor is aware that propionic acid is readily metabolized via propionyl coenzyme A by carboxylation to methylmalonyl CoA which is converted to succinyl CoA, an intermediate in the tricarboxylic acid cycle.

Propionates are generally recognized as safe, cheap, and readily available. For all the above reasons, calcium propionate was selected as the microbistat to test in this individual in an attempt to demonstrate the practical feasibility of reducing excess flatulence by the intracolonic delivery of an appropriate microbistat to inhibit excessive microbial fermentation in the large intestine.

EXAMPLE

The pectin coating mix (PCM) was prepared by blending 10 g high methoxyl citrus pectin with 2.0 mL distilled water to give a free flowing powder. A quantity of 300 mg PCM was distributed evenly over the bottom of a compression well cylinder (16 mm inner diameter) of a manual tablet press. A tubular sleeve (12 mm outside diameter, 10 mm inside diameter) was centered on top of the PCM powder. A quantity of 400 mg of PCM was evenly placed into the 2 mm space between the sleeve and the compression cylinder wall. Next, 350 mg of powder of the hemicalcium salt of propionic acid (CP) was placed in the tubular sleeve. An additional quantity of 300 mg PCM was evenly distributed over the top of the outer PCM and CP. The finished tablet was then produced by direct compression. This compressed tablet was designated CP1.

At the end of the 3 week baseline data collection phase on the pioneer subject, oral ingestion of pectin-coated calcium propionate tablets was begun. Initially, one tablet was consumed before each meal, 3 tablets per day for the first 2 days. The first 7 tablets consumed were made as described above, except 3×400 mg portions of PCM were used to make the tablets. The CP1 tablets were started and used throughout the rest of the study.

After the first 3 days, CP1 tablet ingestion was reduced to one tablet per day taken just before the first meal of the day. After 4 days of a once-per-day dose, intake of CP1 tablets was reduced to a twice per week dosage schedule and continued on this schedule for the remainder of the test.

During the period of this study CP1 treatment reduced the average number of daily flati from 19 in the baseline period to a daily average of 8 during the treatment period, for an overall 58% total reduction. During the baseline period daily flatus frequency ranged from 4 to 41. The daily range during CP1 treatment was from 3 to 15. The individual also noted reduced incidence of abdominal pain and discomfort during the CP1 treatment period.

Flatus periodicity was still apparent during CP1 treatment. However the peak to trough heights were markedly reduced by CP1. Average peak height was 12 (versus 32 for the baseline period), and trough height was 6 (versus 9 during the baseline). Therefore, trough to peak heights were 23 and 6 during the baseline and treatment periods, respectively.

An additional example is prepared as described above in "Detailed Description of the Invention: Example" except that, instead of CP, propylparaben is placed in the tubular sleeve to produce a tablet consisting of 1000 mg PCM coating plus a core of 20 mg propylparaben.

Another example is prepared as described above in "Detailed Description of the Invention: Example" except that, instead of CP alone, a mixture of CP and propylparaben is placed in the tubular sleeve to produce a tablet consisting of 1000 mg PCM coating plus a core of 250 mg CP and 20 mg propylparaben.

Another additional example is prepared as described above in "Detailed Description of the Invention: Example" except that, instead of CP alone, a mixture of CP, propylparaben, and simethicone is placed in the tubular sleeve to produce a tablet consisting of 1000 mg PCM coating plus a core of 80 mg simethicone, 250 mg CP, and 20 mg propylparaben.

Still another additional example is prepared as described above in "Detailed Description of the Invention: Example" except that, instead of CP, potassium sorbate is placed in the tubular sleeve to produce a tablet consisting of 1000 mg PCM coating plus a core of 250 mg potassium sorbate.

Yet another additional example is prepared as described above in "Detailed Description of the Invention: Example" except that, instead of CP, a mixture of potassium sorbate, propylparaben, and simethicone is placed in the tubular sleeve to produce a tablet consisting of 1000 mg PCM coating plus a core of 80 mg simethicone, 250 mg potassium sorbate, and 20 mg propylparaben. Another additional example is prepared as described above in "Detailed Description of the Invention: Example" except that, instead of pectin, cellulose is blended with water to form a cellulose coating mix (CCM), and the CCM is employed instead of PCM to form the coating for a tablet consisting of 1000 mg cellulose coating plus a core of 350 mg CP.

Another example is prepared by blending propylparaben, microcrystalline cellulose, and calcium acetate in a ratio of 40:50:10 in a mixer, and then adding 0.7 parts (by mass) 1% (w/w) sodium carboxymethylcellulose. The mixture is then extruded, spheronized, and dried. The resultant spherical cores are mixed in a 4% aqueous solution of pectin with stirring to form pectin-coated pellets.

Another example is prepared by first preparing a matrix of chondroitin sulfate cross-linked by diaminododecane, with said cross-linking catalyzed by dicyclohexylcarbodiimide. An agglomeration is then made by mixing the cross-linked chondroitin sulfate with CP in a mass ratio of 9:1. A tablet is then formed by compression of said mixture in a manual press.

It is to be understood that the invention is not to be limited to the exact details of operation, or to the exact compositions, methods, procedures, or embodiments shown and described, as obvious modifications and equivalents will be apparent to one skilled in the art, and the invention is therefore to be limited only by the full scope which can legally be accorded to the appended claims.

I claim:

1. An antiflatulent composition consisting essentially of:

a polysaccharide;

a preservative; and a pharmaceutically acceptable carrier or diluent, wherein the mass ratio of preservative to polysaccharide is at least 1:50 and wherein:

(a) the polysaccharide is selected from the group, consisting of pectin, pectinic acid, high methoxyl pectin, low methoxyl pectin, amidated pectin, and (b) the preservative is selected from the group consisting of acetic acid, benzoic acid, butyric acid, citric acid, lactic acid, propionic acid, sorbic acid, syringic acid, and vanillic acid; the sodium, potassium and calcium salts of each of said acids; butylated hydroxyanisole and butylated hydroxytoluene.

2. An antiflatulent composition consisting of, by mass:

about 25% hemicalcium salt of propionic acid;

from about 60% to about 75% high methoxyl citrus pectin; and from about 0% to about 15% water.

3. A method of treating or lessening flatulence in a vertebrate comprising the step of administering to said vertebrate an effective quantity of the antiflatulent composition of claim 1.

4. A method of treating or lessening flatulence in a vertebrate comprising the step of administering to said vertebrate an effective quantity of the antiflatulent composition of claim 2.

* * * * *